(12) United States Patent  (10) Patent No.: US 8,966,992 B2
Arzoumanidis et al.  (45) Date of Patent: Mar. 3, 2015

(54) LOAD FRAME ASSEMBLY

(75) Inventors: G. Alexis Arzoumanidis, Glenview, IL (US); Charles Meade Spellman, Chicago, IL (US); Vishaal B. Verma, Evanston, IL (US)

(73) Assignee: Psylotech, Evanston, IL (US)

( * ) Notice: Subject to any disclaimer, the term of this patent is extended or adjusted under 35 U.S.C. 154(b) by 245 days.

(21) Appl. No.: 13/619,874

(22) Filed: Sep. 14, 2012

(65) Prior Publication Data

US 2013/0125661 A1    May 23, 2013

Related U.S. Application Data

(60) Provisional application No. 61/534,868, filed on Sep. 14, 2011.

(51) Int. Cl.
  *G01B 7/16*    (2006.01)
  *G01N 3/02*    (2006.01)
  *G01B 5/30*    (2006.01)

(52) U.S. Cl.
  CPC ... *G01N 3/02* (2013.01); *G01B 5/30* (2013.01)
  USPC .......................................................... 73/781

(58) Field of Classification Search
  CPC ............. G01N 3/08; G01N 1/00; G01B 5/30; G01B 7/18
  USPC .................... 73/760, 781, 788, 845
  See application file for complete search history.

(56) References Cited

U.S. PATENT DOCUMENTS

| | | | | |
|---|---|---|---|---|
| 4,478,086 | A | * | 10/1984 | Gram ............................... 73/781 |
| 5,092,179 | A | * | 3/1992 | Ferguson ........................ 73/790 |
| 5,195,378 | A | * | 3/1993 | Ferguson ........................ 73/790 |
| 5,581,040 | A | * | 12/1996 | Lin .................................. 73/857 |
| 5,739,411 | A | * | 4/1998 | Lee et al. ..................... 73/12.13 |
| 5,948,994 | A | * | 9/1999 | Jen et al. ......................... 73/856 |
| 6,321,826 | B1 | * | 11/2001 | Fink et al. ..................... 164/316 |
| 6,938,494 | B2 | * | 9/2005 | Takada et al. ................... 73/760 |
| 2009/0026645 | A1 | * | 1/2009 | Tsuda et al. ................. 264/40.1 |
| 2012/0146260 | A1 | * | 6/2012 | Murata et al. .............. 264/328.1 |

* cited by examiner

*Primary Examiner* — Max Noori
(74) *Attorney, Agent, or Firm* — The Watson I.P. Group, PLC; Jovan N. Jovanovic; Vladan M. Vasiljevic (57) ABSTRACT

A load frame assembly including a frame assembly, a servomotor, an actuator, a first crosshead assembly, a second crosshead assembly, a load frame and a displacement sensor. The servomotor is coupled to the frame and includes a control system. The actuator is coupled to the first crosshead assembly and provides for moving the first crosshead assembly relative to the frame assembly. The actuator comprises a ball screw assembly having a ball screw and a ball screw nut. The load frame is coupled to one of the crosshead assemblies. The displacement sensor is associated with the frame assembly and is configured to measure displacement by the crossheads relative to the frame assembly.

13 Claims, 10 Drawing Sheets

LOAD FRAME ASSEMBLY

CROSS-REFERENCE TO RELATED APPLICATION

This application claims priority from U.S. Prov. Pat. App. Ser. No. 61/534,868 filed Sep. 14, 2011, entitled, Sensing Equipment, Software And Methods Associated Therewith, the entire specification of which is hereby incorporated by reference in its entirety.

BACKGROUND OF THE DISCLOSURE

1. Field of the Disclosure

The disclosure relates in general to materials testing equipment, and more particularly, to a load frame assembly, typically for use in association with a microscope for under microscope materials testing and digital image correlation. The particular load frame is not limited to use therewith.

2. Background Art

The use of a load frame to test material properties is well known in the art. Generally, load frames are utilized to apply a force to a specimen, and sensors can determine the physical material changes to the specimen.

There is a desire to utilize under microscope materials testing, of polymers, composite materials, fibers, mechanical structures, films, ceramics, metals, among other substances. Such systems utilize a microscope, a digital camera with a digital image correlation software which can monitor a displacement field to, for example, sub-pixel resolution. In certain embodiments, a 0.1 pixel resolution of displacement can be achieved with such software, and even approaching 0.01 pixel resolution of displacement.

What has become necessary in such testing systems, is a load frame which can be carefully controlled, and from which measurements can accurately be determined based upon the application of a load to a specimen. Among other difficulties, analysis of such small samples is inherently difficult. At such a scale, even minor losses or negative equipment effects (tolerances, etc.) can have a large impact on test results. Additionally, the ability to control micro and nano movements and relatively small loads and displacements accurately has proven very difficult.

It is an object of the present disclosure to provide a load frame assembly which is suitable for under microscope applications.

It is another object of the present disclosure to provide a load frame assembly that overcomes the shortcomings of the prior art.

It is another object of the disclosure to improve materials testing data through an improved load frame assembly.

These objects as well as other objects of the present invention will become apparent in light of the present specification, claims, and drawings.

SUMMARY OF THE DISCLOSURE

The disclosure is directed to a load frame assembly comprising a frame assembly, a servomotor, an actuator assembly, a first crosshead assembly, a second crosshead assembly, a load frame and a displacement sensor. The servomotor is coupled to the frame assembly and has a control system. The actuator assembly has a ball screw assembly, with a ball screw and a ball screw nut rotatably coupled to the ball screw. One of the ball screw and the ball screw nut are coupled to the frame assembly to preclude linear movement therealong, and coupled to the servomotor to facilitate rotation thereof about an axis. The first crosshead assembly is coupled to one of the ball screw and the ball screw nut. The first crosshead assembly is slidably positionable within the frame assembly so as to move linearly therealong. Additionally, the first crosshead assembly is mounted so as to substantially preclude the crosshead from any rotative movement relative to the frame assembly. The second crosshead assembly is spaced apart from the first crosshead assembly and coupled to the frame assembly. A specimen may be configured at a first end to move with the first crosshead assembly and at a second end to move with the second crosshead assembly. The load frame is coupled to one of the first and second crosshead assemblies. The displacement sensor is associated with the frame assembly and at least one of the first and second crossheads. The displacement sensor is configured to measure displacement of at least one of the first and second crossheads with which the displacement sensor is associated relative to the frame assembly.

In a preferred embodiment, the frame assembly further includes a first side member and a second side member, and a first end member. The actuator assembly is coupled to the first end member, with the first and second crosshead assemblies being bound between the first and second side members.

In another preferred embodiment, at least one of the load cell and the displacement sensor is coupled to the control system of the servomotor to provide feedback as to the position of the respective one of the first and second crosshead.

In another preferred embodiment, the second crosshead is fixed to the frame assembly and precluded from relative movement.

In another embodiment, the system further includes a first gripping arm assembly coupled to the first crosshead assembly and a second gripping arm assembly coupled to the second crosshead assembly.

In one such preferred embodiment, the first gripping arm assembly includes a grip dovetail pin and the first gripping arm assembly includes an upper gripping arm and a lower gripping arm couplable to the upper gripping arm. At least one of the upper gripping arm and the lower gripping arm includes a grip dovetail configured to interface with the grip dovetail pin coupling the respective gripping arm thereto.

In another preferred embodiment, the second gripping arm assembly includes a grip dovetail pin and the second gripping arm assembly includes an upper gripping arm and a lower gripping arm couplable to the upper gripping arm. At least one of the upper gripping arm and the lower gripping arm includes a grip dovetail configured to interface with the grip dovetail pin coupling the respective gripping arm thereto.

In another embodiment, each of the upper and lower gripping arms of the first gripping arm assembly include a dovetail structurally configured to engage the grip dovetail pin of the first crosshead assembly.

In a preferred embodiment, each of the upper and lower gripping arms of the second gripping arm assembly include a dovetail structurally configured to engage the grip dovetail pin of the second crosshead assembly.

Preferably, the first gripping arm assembly and the second gripping arm assembly are vertically adjustable.

In a preferred embodiment, the displacement sensor comprises a capacitive sensor, wherein displacement of the respective at least one of the first crosshead and second crosshead results in a change in capacitance.

In another preferred embodiment, the load frame further includes a second servomotor and a second actuator. The second servomotor is coupled to the frame assembly. The second actuator assembly has a ball screw assembly, with a ball screw and a ball screw nut rotatably coupled to the ball screw. One of the ball screw and the ball screw nut is coupled to the frame assembly to preclude linear movement thereal-ong. It is also coupled to the second servomotor to facilitate rotation thereof about an axis. The second crosshead assembly is coupled to one of the ball screw and the ball screw nut of the second actuator assembly.

In another preferred embodiment, at least one of the load cell and the displacement sensor is coupled to the control system of the second servomotor to provide feedback as to the position of the respective one of the first and second crosshead.

BRIEF DESCRIPTION OF THE DRAWINGS

The disclosure will now be described with reference to the drawings wherein:

FIG. 7a of the drawings is a perspective view of the first and second gripper arm assemblies, showing, in particular, the gripper arm assemblies coupled to a specimen, and FIG. 7b of the drawings is a perspective view of the specimen attached by way of a pin to a lower gripping arm of the first gripper arm assembly;

DETAILED DESCRIPTION OF THE DISCLOSURE

While this invention is susceptible of embodiment in many different forms, there is shown in the drawings and described herein in detail a specific embodiment with the understanding that the present disclosure is to be considered as an exemplification and is not intended to be limited to the embodiment illustrated.

It will be understood that like or analogous elements and/or components, referred to herein, may be identified throughout the drawings by like reference characters. In addition, it will be understood that the drawings are merely schematic representations of the invention, and some of the components may have been distorted from actual scale for purposes of pictorial clarity.

Figure 1:
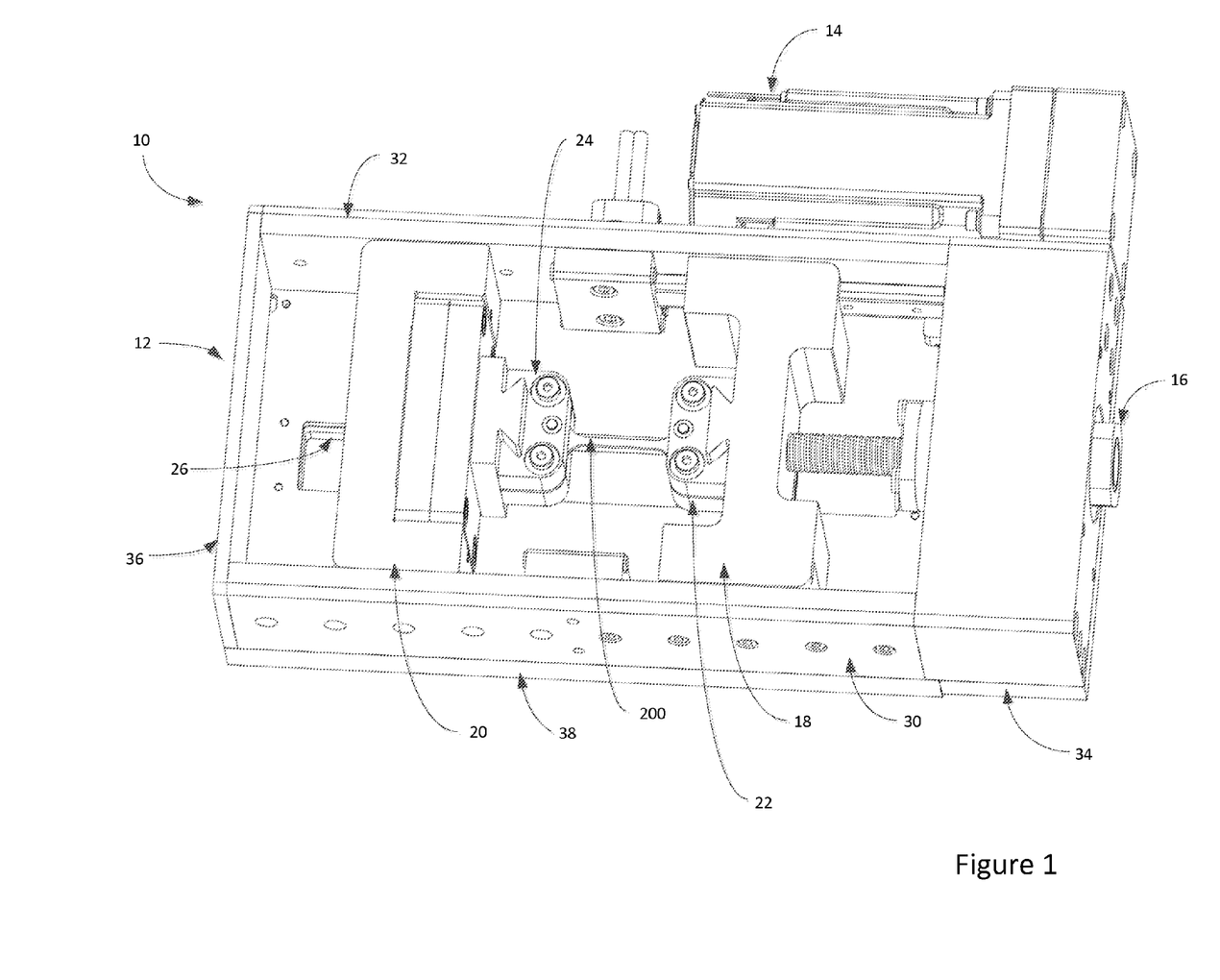
FIG. 1 of the drawings is a perspective view of an embodiment of the load frame assembly of the present disclosure.

Referring now to the drawings and in particular to FIG. 1, load frame assembly 10 is shown generally at 10. It is contemplated that such a system has, for example, a 25 nm resolution and a 50 mm stroke, although such performance characteristics are not to be limiting, but only exemplary. For example, with optimized microscope optics, a displacement field can be monitored to a 0.1 pixel resolution, if not better. The system is well suited for use in association with all types of materials. Indeed, the materials with which the assembly is utilized is not to be deemed limiting, and is for exemplary purposes.

With reference to FIG. 1, the load frame assembly 10 is shown as including frame assembly 12, servomotor 14, actuator assembly 16, first crosshead assembly 18, second crosshead assembly 20, first gripper arm assembly 22, second gripper arm assembly 24 and displacement sensor 26. The frame assembly 12 comprises a plurality of components that are coupled together to provide a rigid frame upon which the other components can be coupled, while limiting any relative movement of the components vis-à-vis each other. The frame assembly includes first side member 30, second side member 32, first end member 34, second end member 36 and bottom member 38. The members may be formed from a single monolithic material, and certain members may be integrally formed with other members. In other instances, the members may comprise different components that are coupled together. In the embodiment shown, structural rigidity is enhanced, in part, by the rigid bottom member to which the other components are coupled.

Figure 2:
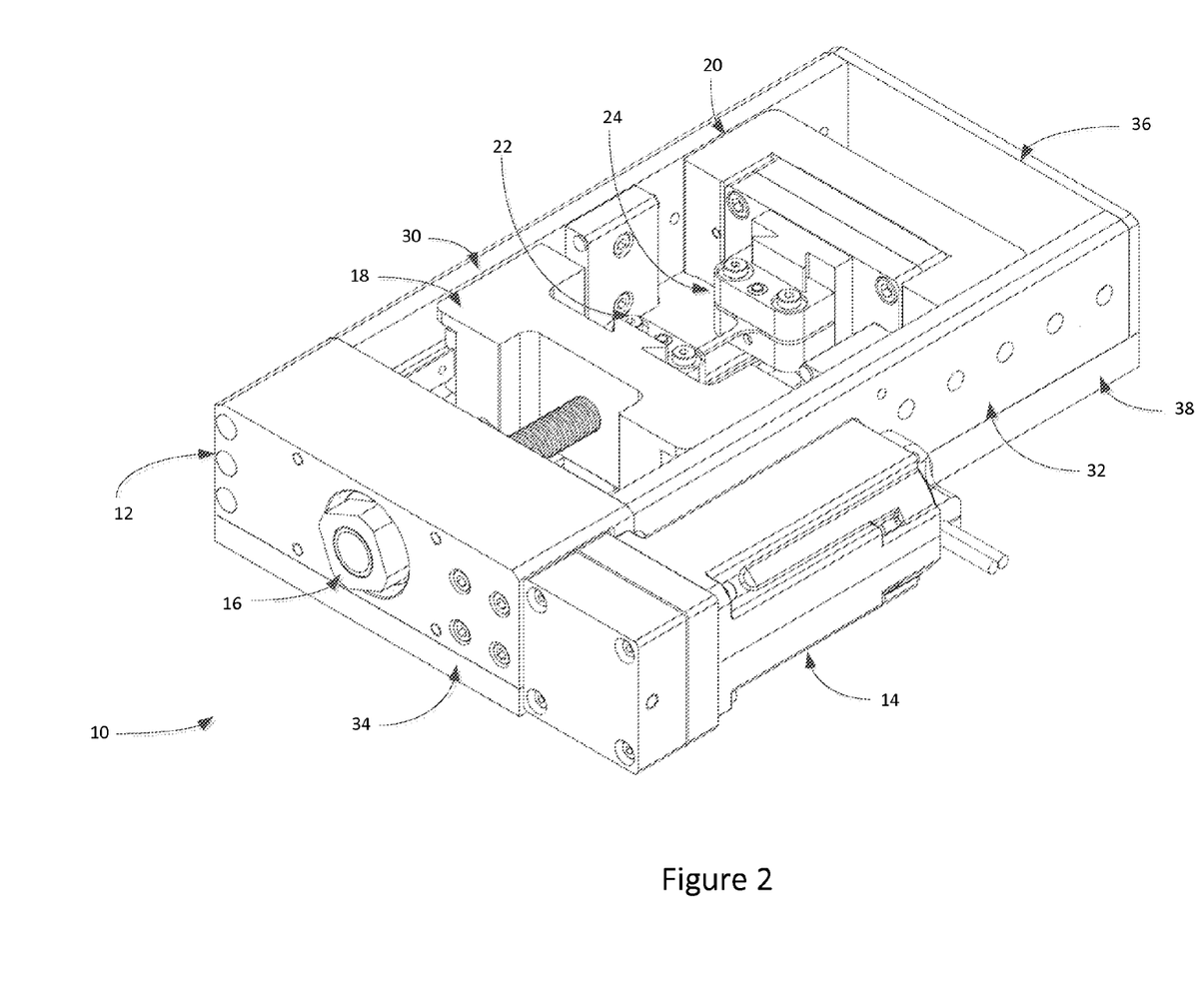
FIG. 2 of the drawings is a perspective view of an embodiment of the load frame assembly of the present disclosure.
Figure 5:
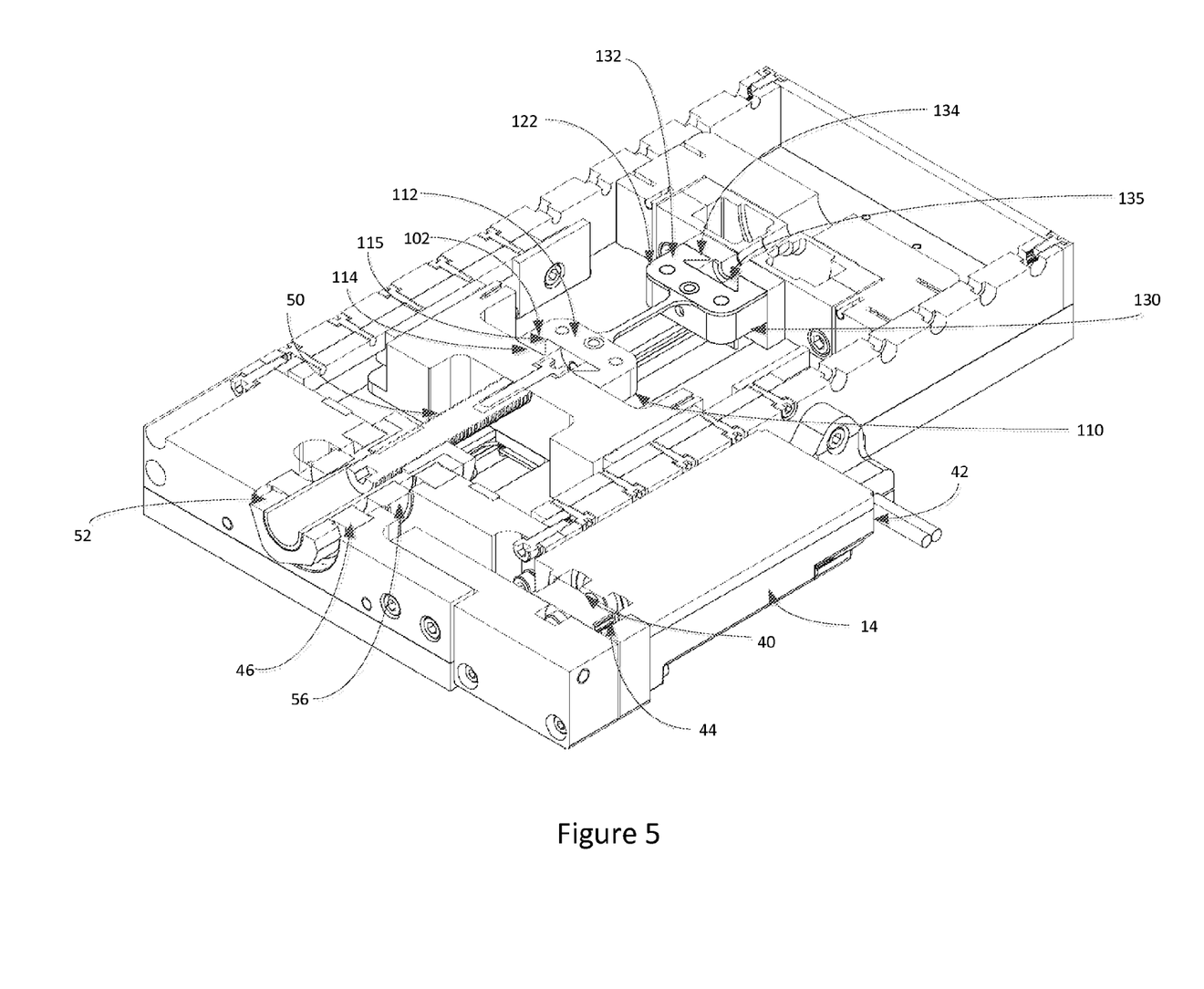
FIG. 5 of the drawings is a perspective view of an embodiment of the load frame assembly of the present disclosure showing the actuator assembly and the servomotor, by removing the housings covering the same for purposes of clarity.

The servomotor 14 is shown in FIGS. 1, 2 and 5, collectively as being coupled to the first side member and/or the first end member 34, and/or the bottom member 38. The servomotor 14 includes output shaft 40 having cogged sprocket 44 and control system 42. In the embodiment shown, the cogged sprocket is configured to receive a belt to couple the same to the actuator. In other embodiments, a direct drive is contemplated, as well as other gear driven solutions. The control system provides movement control for the servomotor 14 and incorporates feedback, as will be explained below, including feedback from the displacement sensor 26 and/or from the load cell 82.

The actuator assembly 16 is shown in FIGS. 1, and 5, collectively as comprising ball screw assembly 46. The ball screw assembly includes ball screw 50, ball screw nut assembly 52, and belt pulley 56. The belt pulley 56 is coupled to the cogged sprocket 44 by way of a belt (not shown). The ball screw nut assembly 52 is rotatably coupled to the frame assembly 12, so as to spin about an axis of rotation, however, the ball screw nut assembly is transversely fixed in its orientation so as to be precluded from liner movement relative to the frame assembly. As such, rotational movement imparted by the servomotor 14 is converted to linear movement of the ball screw 50, which, as will be explained below, linearly displaces the crosshead 50. In other embodiments, the other of the ball screw nut and the ball screw may be precluded from linear movement relative to the frame assembly.

Figure 3:
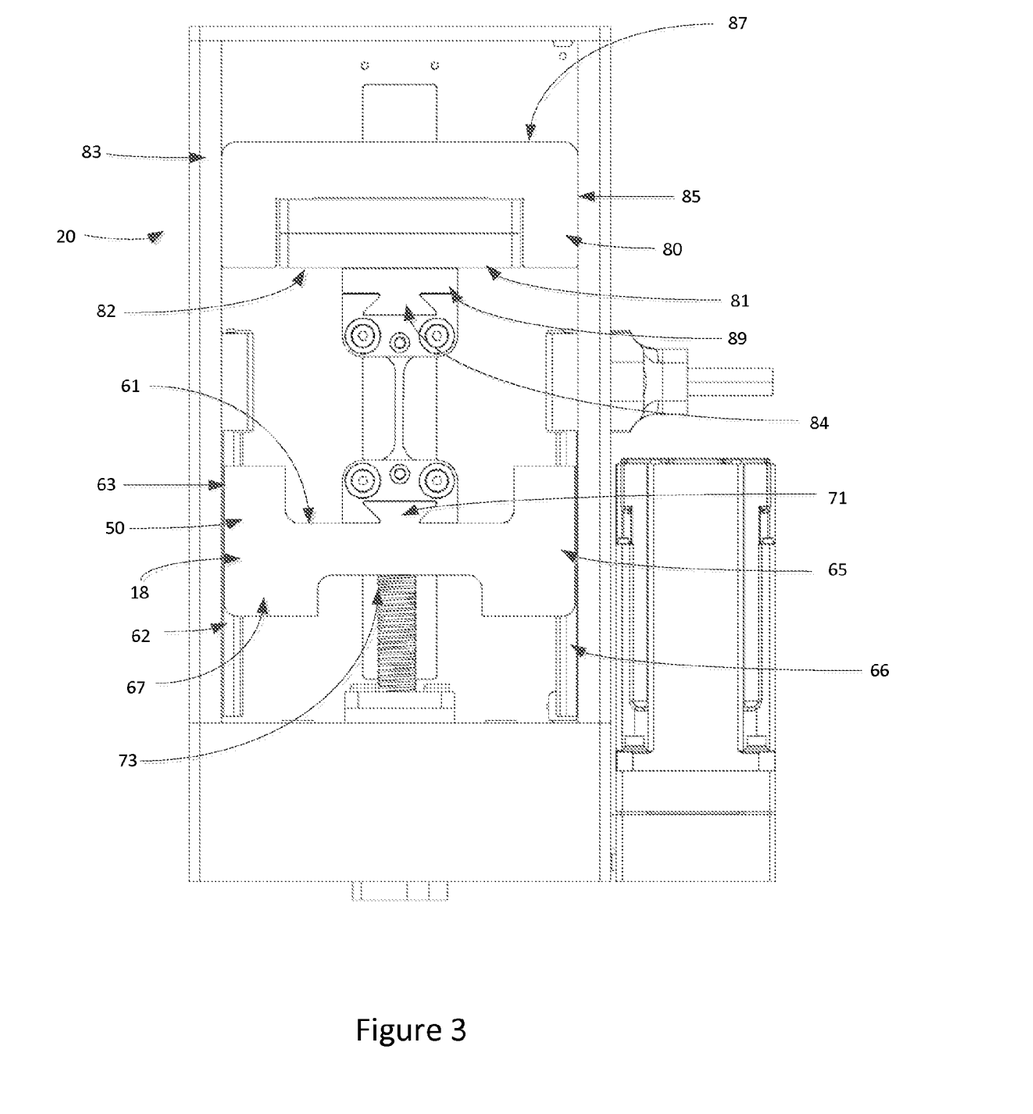
FIG. 3 of the drawings is a top plan view of an embodiment of the load frame assembly of the present disclosure.
Figure 6:
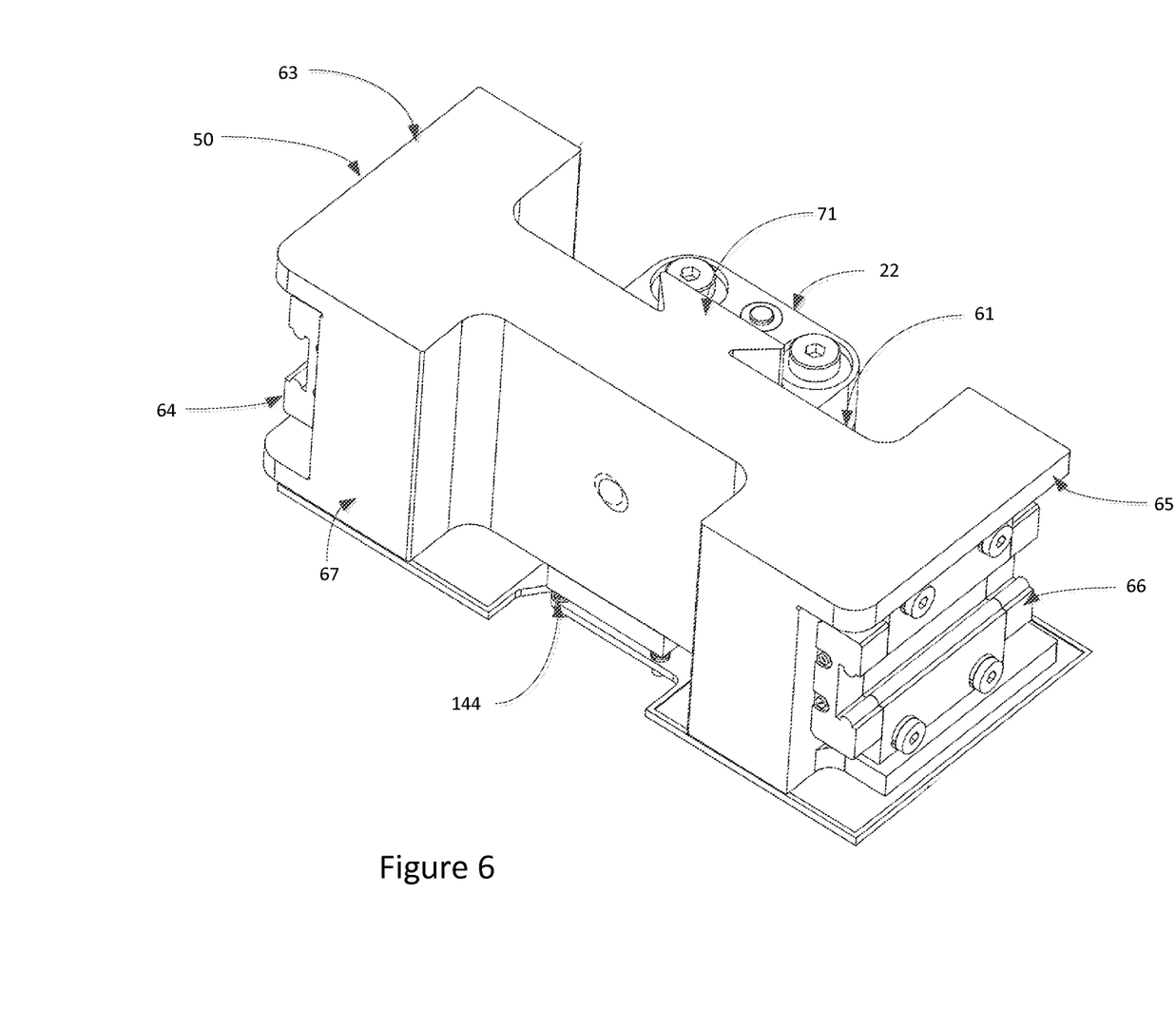
FIG. 6 of the drawings is a perspective view of the first crosshead assembly together with the first gripper arm assembly and the central plate assembly of the displacement sensor.

The first crosshead assembly 18 is shown in FIGS. 3 and 6 as comprising crosshead 50, first side rail 62, first side carriage 64, second side rail 66 and second side carriage 68. The crosshead 50 spans between the first side member 30 and the second side member 32. The crosshead 50 includes inner side 60, first side 63, second side 65, and outer side 67. Generally, the crosshead comprises a stable platform upon which to couple the first gripper assembly, and, in turn, the first end of the specimen. The inner side includes grip dovetail pin 71. As will be explained below, the first gripper arm assembly is coupled to the grip dovetail pin 71. The outer side 67 includes opening 73, through which the ball screw 50 is extended.

The first side rail 62 is fixedly coupled to the first side member 30 and the second side rail 66 is fixedly coupled to the second side member 32. The first side carriage 64 is fixedly coupled to the first side 63 of the crosshead 50. The first side carriage 64 is configured to move linearly along the first side rail. The second side carriage 68 is coupled to the second side 65 of the crosshead 50, and is configured to move linearly along the second side rail. The two side rail and side carriage configurations facilitate the strict linear movement of the crosshead through movement of the ball screw 50. The side carriage comprises a linear bearing with very low friction. In other embodiments, these linear guides that insure linear travel of the crosshead may comprise flexures, air bearings, among others. Significantly, the desire is to maintain linear movement of the crosshead, and to preclude rotational movement of the crosshead relative to the frame assembly.

The second crosshead assembly 20 is shown in FIG. 3 as comprising crosshead 80 and load cell 82. The crosshead 80, in the embodiment shown, is generally fixed relative to the frame assembly 12. For example, the crosshead 80 may be coupled to the first side member 30, the second side member 32 and/or the bottom surface member 38. The load cell 82 is coupled to the inner side 81 of the crosshead 80. In the embodiment shown, the crosshead includes a slot extending therethrough, with the load cell 82 fitting within the slot, and being coupled thereto. The grip mount bracket 89 is coupled to the load cell 82 and includes dove tail pin 84 coupled thereto. Thus, the load cell 82 is positioned between the grip mount bracket 89 and the inner side 81 of the crosshead (which is fixed to the frame assembly 12). It will be understood that the load cell may comprise a three axis load cell (which may be of high resolution), such that moments can also be analyzed in addition to force loadings.

Figure 7:
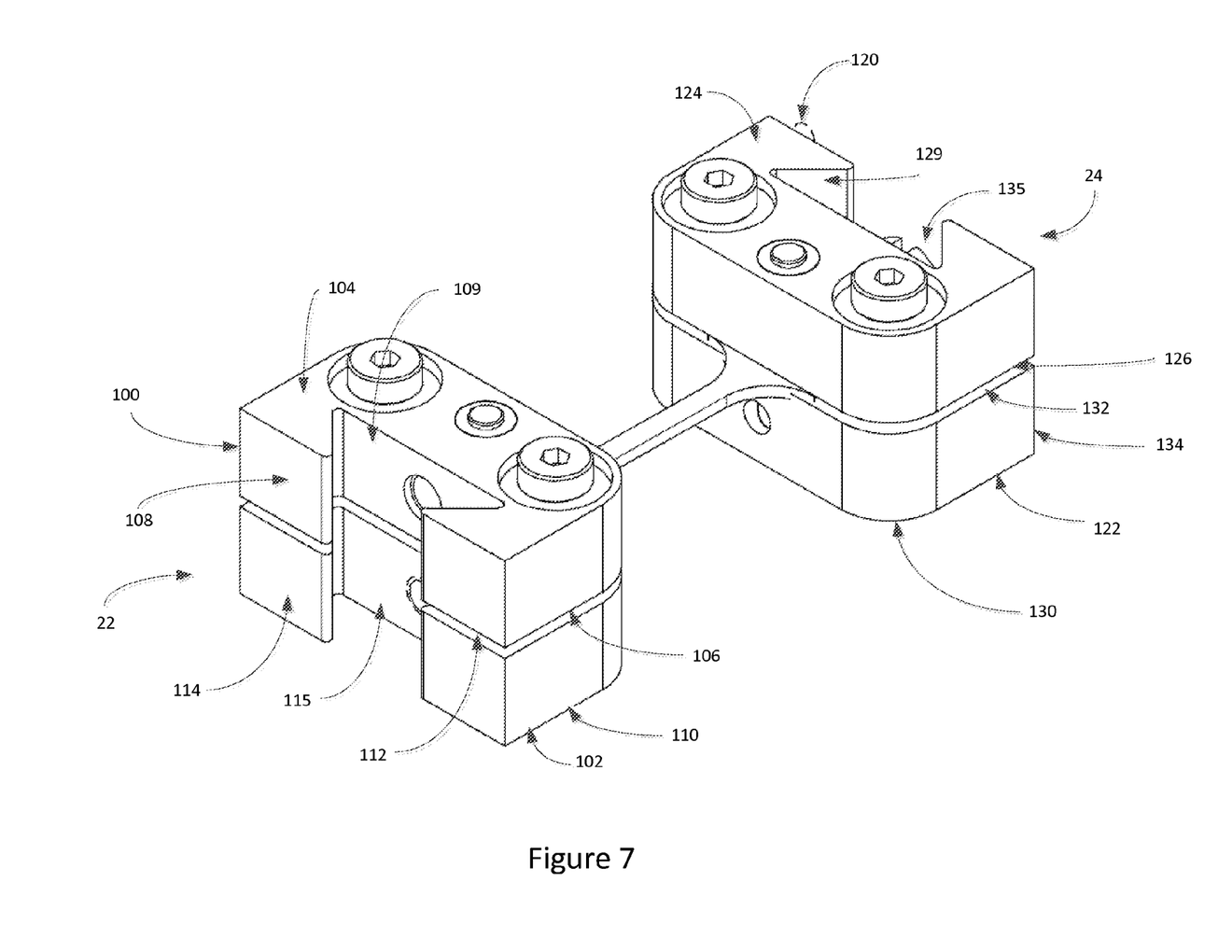

The first gripper arm assembly 22 is shown in FIG. 7a as comprising upper gripper arm 100 and lower gripper arm 102. The upper gripper arm 100 includes outer surface 104, inner surface 106 and back side 108. The back side 108 includes dovetail 109. The lower gripper arm 102 generally comprises a substantial mirror image of the upper gripper arm 100, and includes outer surface 110, inner surface 112 and back side 114. The back side 114 includes dovetail 115. As is shown in the Figures, the lower gripper arm and the upper gripper arm are configured in a stacked orientation, with the inner surface 106 of the upper gripper arm 100 and the inner surface 112 of the lower gripper arm facing each other. Fasteners and the like are provided which facilitate the clamping or fastening of the upper gripper arm to the lower gripper arm. A specimen end can be positioned between the inner surfaces of the upper and lower gripper arms wherein the two can be clamped together to sandwich the specimen therebetween (utilizing a Bellville washer) and screws, which are typically uniformly positioned. Additional pins and other structures may be disposed on the inner surfaces to aid in the retention of the specimen by the gripper arms (FIG. 7b). The upper and lower gripper arms are symmetric so as to maintain the specimen in a plane, so as to keep the same in focus. In other embodiments, the upper and lower gripper arms may comprise a basis for the attachment of different types of material specimen holders.

The upper and lower gripper arms are coupled to the inner side 61 of crosshead 50. In particular, dovetail 109 of the upper gripper arm and dovetail 115 of the lower gripper arm are slid into the grip dovetail pin 61 of the crosshead 50.

The second gripper arm assembly 24 is shown in FIG. 7a as comprising upper gripper arm 120 and lower gripper arm 122. The upper gripper arm 120 includes outer surface 124, inner surface 126 and back side 128. The back side 128 includes dovetail 129. The lower gripper arm 122 generally comprises a substantial mirror image of the upper gripper arm 120, and includes outer surface 130, inner surface 132 and backside 134. The back side 134 includes dovetail 135. As is shown in the Figures, the lower gripper arm and the upper gripper arm are configured in a stacked orientation, with the inner surface 126 of the upper gripper arm 120 and the inner surface 132 of the lower griper arm 122 facing each other. Fasteners and the like are provided which facilitate the clamping or fastening of the upper gripper arm to the lower gripper arm. A specimen can be positioned between the inner surfaces of the upper and lower gripper arms (often interfacing an opening on the specimen with a pin on the gripper arm) wherein the two can be clamped together to sandwich the specimen therebetween. Additional pins and other structures may be disposed on the inner surfaces to aid in the retention of the specimen by the gripper arms.

The upper and lower gripper arms of the second gripper arm assembly 24 are coupled to the inner side 81 of the crosshead 80. More particularly, dovetail 129 and dovetail 135 are slidably coupled into the grip dovetail pin 84 of the crosshead 80. Manual centering can be achieved therefrom.

Figure 4:
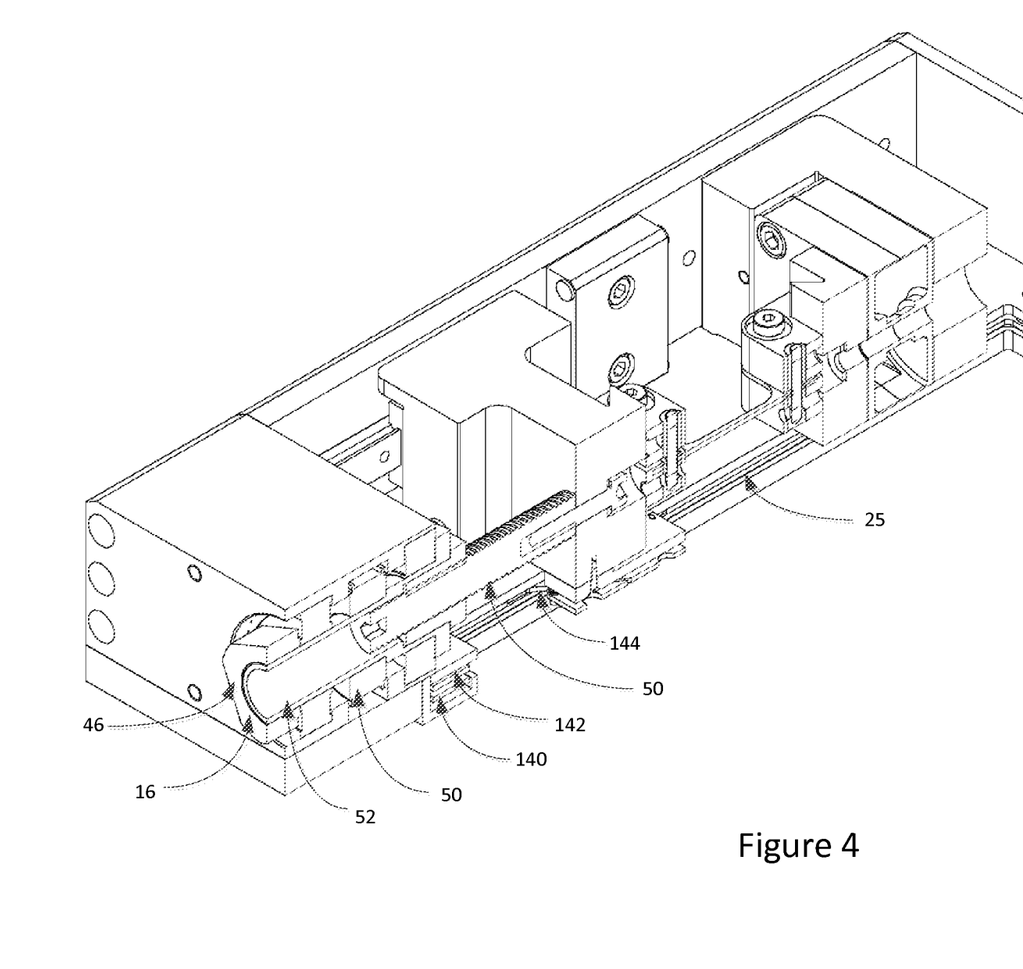
FIG. 4 of the drawings is an exploded perspective view of the sensor assembly for use in association with the present disclosure.

The displacement sensor 26 is shown in FIG. 4 (in cooperation with FIG. 1) as comprising outer capacitive plate 140 and inner capacitive plate 142, and, central plate assembly 144. The outer and inner capacitive plates 140, 142 are fixed to the frame assembly, and in the embodiment shown, fixed to the bottom surface member 38. The central plate assembly 144 may comprise multiple independent plates, or a single plate, connected to the crosshead 50, such that the central plate assembly moves relative to the outer and inner capacitive plates upon movement of the crosshead 50. It will be understood that movement of the central plate assembly 144 alters the capacitance, which can be measured, from which, displacement (or movement) of the crosshead 50 relative to the frame assembly 12 can be determined. Advantageously, in such a configuration, there are no lead wires or other circuitry associated with the moving central plate assembly (coupled to the crosshead), thereby increasing robustness, and providing high sensitivity. Also, by measuring the displacement on the specimen side of the load cell, then any movement of the load cell (which may be on the order of 40 microns), can be taken into account, which in turn increases compliance (which can also be achieved electronically or in the software associated with the system). Other sensors are contemplated for use, including, but not limited to inductive voltage dividers and LVDT's. The displacement sensor can also be a multi-axis sensor.

In operation, the user is first provided with the load frame assembly. It will be understood that the load frame assembly may be coupled to an optical microscope which may include software for digital image processing. Once provided, a specimen for testing is provided. The specimen typically includes an elongated specimen or member, such as specimen which has a first and second end. Generally, the specimen is a substantially planar material (although variations are contemplated) having an upper and lower surface and substantially uniform thickness. Of course, this is merely exemplary, and other embodiments are likewise contemplated.

It is necessary to couple the specimen to the gripper arms. In particular, the first end of the specimen is sandwiched between the upper gripper arm 100 and the lower gripper arm 102 of the first gripper arm assembly 22. Similarly, the second end of the specimen is sandwiched between the upper gripper arm 120 and the lower gripper arm 122 of the second gripper arm assembly 24. Once the specimen is attached to the two gripper arms, the gripper arms can be coupled to the respective first and second crosshead assemblies 18, 20. In particular, the grip dovetail pin 71 is interfaced with the dovetail 109 and the dovetail 115 of the upper and lower gripper arms of the first gripper arm assembly. Similarly, grip dovetail pin 84 of the second crosshead 80 is interfaced with the dovetail 129 and the dovetail 135 of the upper and lower gripper arms of the second gripper arm assembly.

Figure 10:
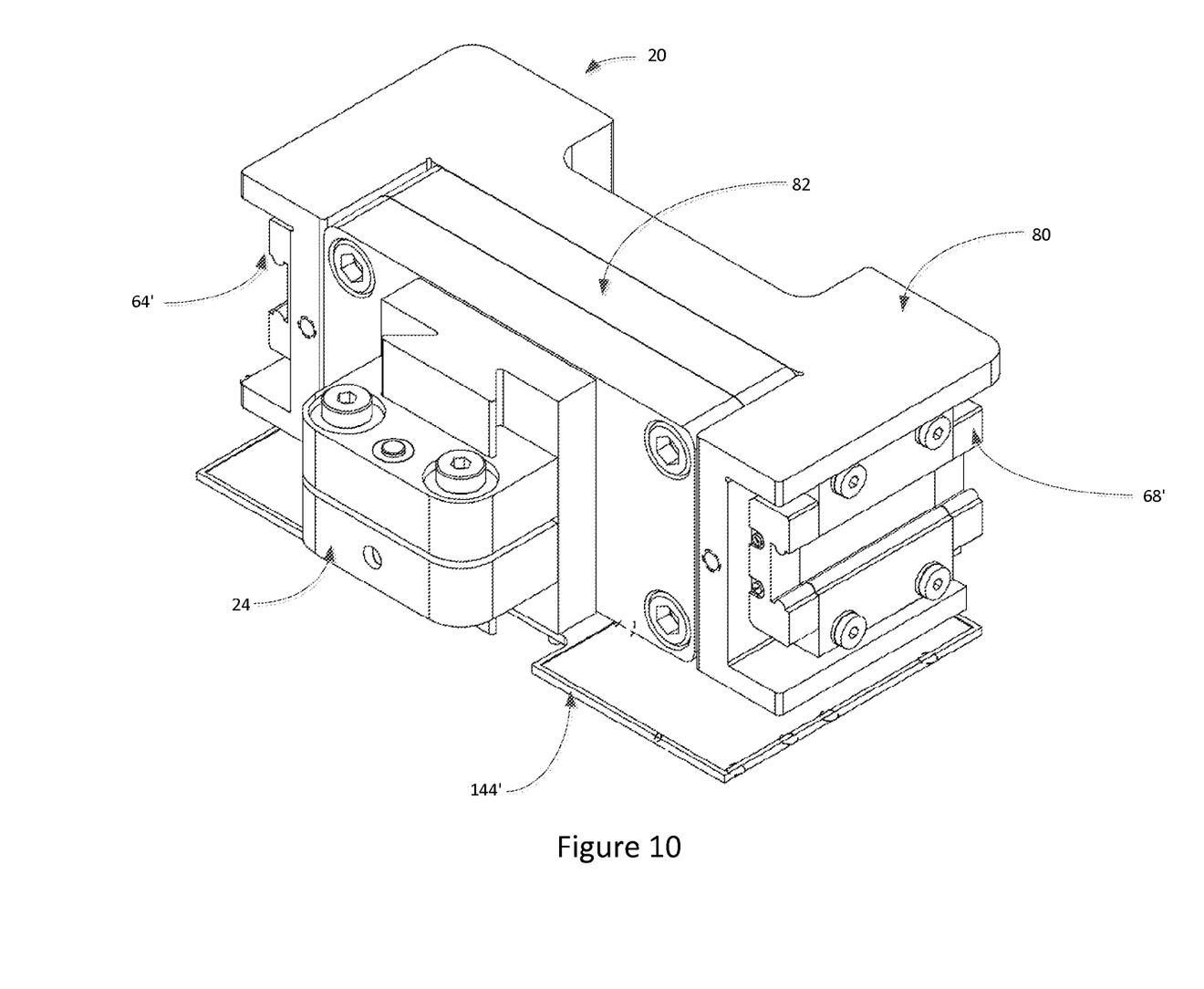
FIG. 10 of the drawings is a perspective view of an embodiment of a vertical adjustment element for use in the present disclosure to maintain the planar and flat configuration of the specimen by adjusting the vertical position of the gripper arms (and in turn the specimen).

It will be understood that in other embodiments, the lower gripper arms 102 and 122 can first be coupled to the respective crosshead 50, 80 first. Subsequently, the specimen can be introduced. The upper gripper arms 100, 120 can then be secured to the respective crosshead. Finally, the upper and lower gripper arms can be secured together sandwiching the specimen therebetween. Finally, the gripper arms can be adjusted vertically with either one of the crosshead assemblies, such that the user can have control over the vertical position of either one of the specimen ends relative to the cross-head. One such manner of adjustment is shown in FIG. 10 as comprising a set screw 97 which can be rotated to move an adjustment plate 98 (or the bottom gripper) to achieve the desired height.

Once secured, the servomotor can be used to displace (or move) the crosshead 50 relative to the frame assembly. In particular, activation of the servomotor by way of control system 42 to rotate the ball screw nut assembly, in turn, moves the ball screw 50?. As the ball screw 50 translates (for example in a direction toward the first side member 30), a tensile load is applied to the specimen. At such time, load cell 82, which is, at the one end fixed to the crosshead 80 and at the other end fixed to the second gripper arm assembly (and to the second end of the specimen), provides data as to the load that has been applied to the specimen. Additionally, the displacement sensor 26 provides data as to the displacement of the crosshead 50 relative to the frame assembly 12.

Advantageously, while it will be understood that the servomotor 14 includes a number of internal sensors and feedback loops to insure movement and position thereof, the displacement sensor 26 and/or the load cell 82 can also be utilized to provide feedback to the servomotor. This is quite advantageous, as the displacement sensor and the load cell are positioned substantially downstream of the servomotor and proximate the specimen. Thus, any frictional effects, axial play affects and other losses of the actuator assembly, the belt system between the servomotor and the actuator assembly, as well as any play in the system can be effectively eliminated, and the servomotor can be controlled by measurements taken of the specimen which inherently takes into account any undesirable losses and effects. It will be understood that in certain embodiments, commutation feedback is provided by a hall effect sensor, and velocity and position can be provided by a linear displacement sensor. As linear displacement is the desired output, so to speak, closed loop control of a linear displacement sensor provides more direct feedback.

It will be understood that in other embodiments, the gripper arms disclosed above can be replaced with, for example, an Arcan fixture which can provide varying configurations and manners in which to couple to a load frame. An Arcan fixture allows for a pure shear position, a pure tension position, as well as mixed mode positions. Such fixtures are well known in the art. In addition, other tension gripper arms (i.e., pin tension, wedge tension) are contemplated for use, as are compression gripper arms, and four point bend gripper arms. Indeed, the disclosure is not limited to any particular configuration.

Figure 8:
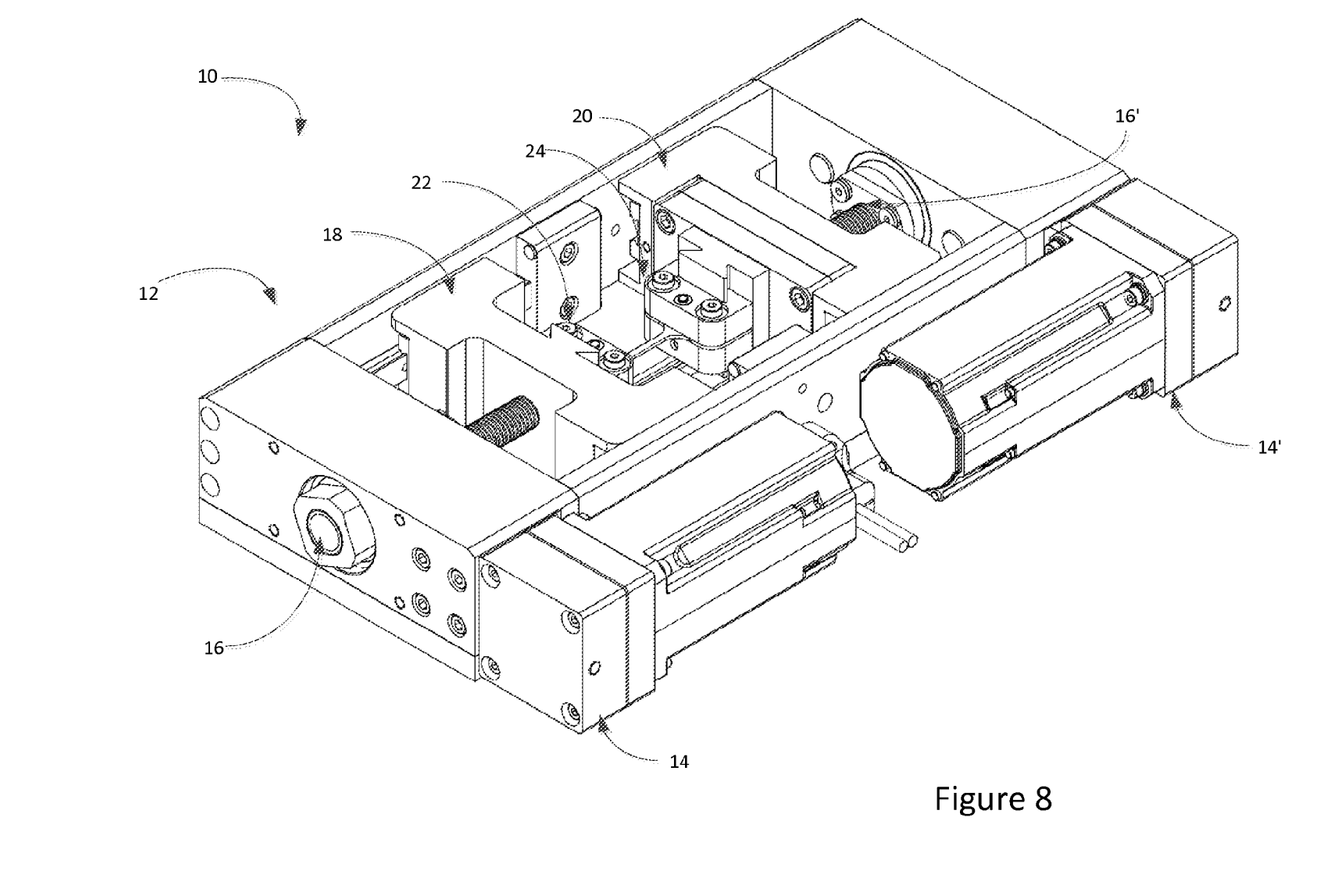
FIG. 8 of the drawings is a perspective view of an embodiment of the load frame assembly of the present disclosure, showing, in particular, independently controlled crosshead assemblies.
Figure 9:
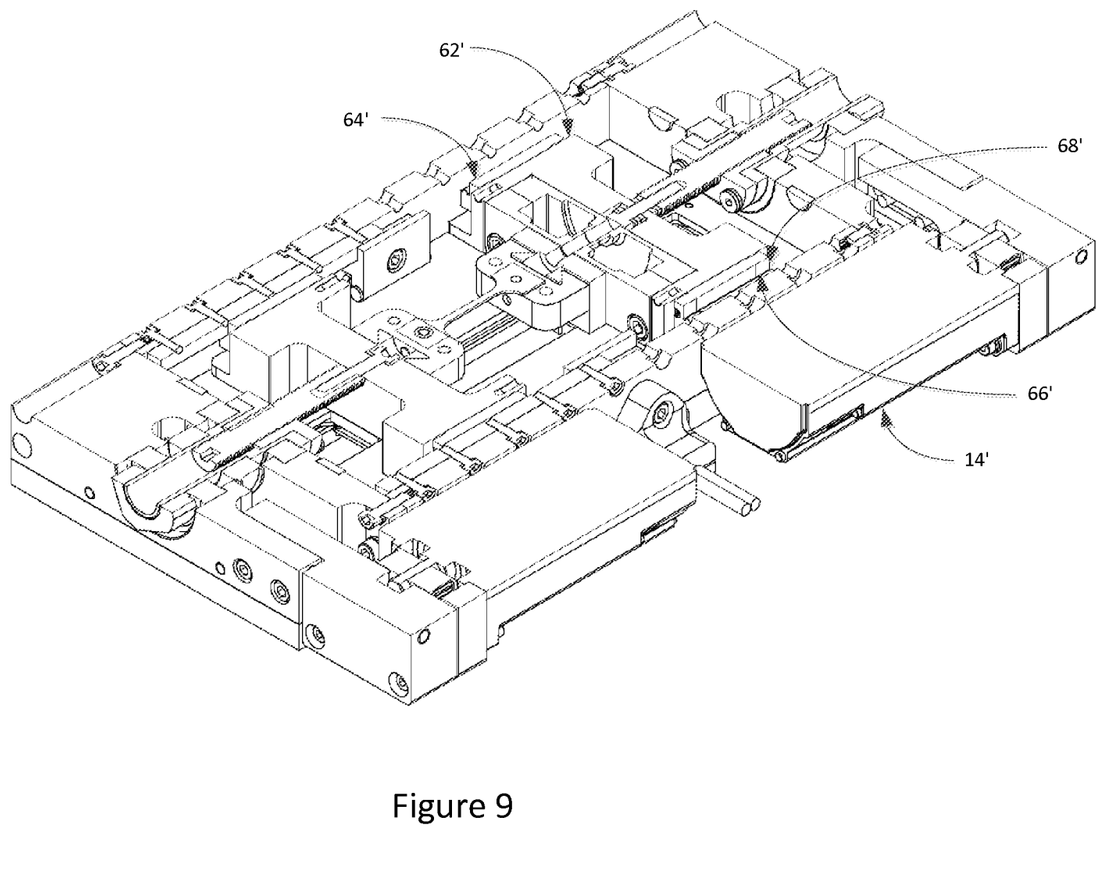
FIG. 9 of the drawings is a perspective view of the second crosshead assembly together with the second gripper arm and the second central plate assembly.

Another embodiment of the load frame assembly 10 is shown in FIGS. 8 and 9. In such a configuration, the second crosshead assembly 20 is structurally configured much like the first crosshead assembly in that it is independently controllable and independently movable relative to the first crosshead assembly 18. More particularly, a second servomotor 14', as well as a second actuator assembly 16' is provided. In addition, the displacement sensor is modified in that the outer capacitive plate and the inner capacitive plate interface with a second central plate assembly 144' so as to provide data as to the movement of the second cross head 80.

Additionally, a second of rails and carriages is supplied to allow the second crosshead to linearly translate relative to the frame assembly. In particular, first side rail 62' is coupled to the first side member 30 and first side carriage 64' is fixedly coupled to the first side 83 of the crosshead 80. Similarly, second side rail 66' is coupled to the second side member 32 and second carriage 68' is fixedly coupled to the second side 85 of the cross head 80. As such, the first and second side carriages are configured to linearly translate along the first and second side rails, respectively.

Such an embodiment is useful, if translation of a specimen that has been loaded is desired, for example, in that the servomotors can cooperate to translate a specimen that has been loaded. In other instances, it may be desirable to actuate one of the servomotors so that the displacement occurs at a desired end of the specimen. It will be understood that the first and second crosshead can move completely independently of each other, or may be related to each other, as desired, so as to accommodate rigid body translation.

It is contemplated that the frame assembly 12 and the second crosshead assembly 20 be configured to be modular, that is, a second servomotor and actuator assembly can be coupled to the frame assembly and the second crosshead assembly without modification of either one of the same.

It will be understood that the load frame 82 may be positioned on either one of the crosshead 50, 80, and that the load cell is positioned on the second crosshead 80 purely for exemplary purposes.

The foregoing description merely explains and illustrates the invention and the invention is not limited thereto except insofar as the appended claims are so limited, as those skilled in the art who have the disclosure before them will be able to make modifications without departing from the scope of the invention.

What is claimed is:

1. A load frame assembly comprising:
 a frame assembly;
 a servomotor coupled to the frame assembly, the servomotor having a control system;
 an actuator assembly having a ball screw assembly, with a ball screw and a ball screw nut rotatably coupled to the ball screw, one of the ball screw and the ball screw nut being coupled to the frame assembly to preclude linear movement therealong, and coupled to the servomotor to facilitate rotation thereof about an axis;
 first crosshead assembly coupled to one of the ball screw and the ball screw nut, the first crosshead assembly slidably positionable within the frame assembly so as to move linearly therealong;
 a second crosshead assembly spaced apart from the first crosshead assembly and coupled to the frame assembly, wherein a specimen may be configured at a first end to move with the first crosshead assembly and at a second end to move with the second crosshead assembly;
 a load frame coupled to one of the first and second crosshead assemblies; and
 a displacement sensor associated with the frame assembly and at least one of the first and second crossheads, the displacement sensor configured to measure displacement of at least one of the first and second crossheads with which the displacement sensor is associated relative to the frame assembly.

2. The load frame assembly of claim 1 wherein the frame assembly further includes a first side member and a second side member, and a first end member, the actuator assembly being coupled to the first end member, with the first and second crosshead assemblies being bound between the first and second side members.

3. The load frame assembly of claim 1 wherein at least one of the load cell and the displacement sensor is coupled to the control system of the servomotor to provide feedback as to the position of the respective one of the first and second crosshead.

4. The load frame assembly of claim 1 wherein the second crosshead is fixed to the frame assembly and precluded from relative movement.

5. The load frame assembly of claim 1 further comprising a first gripping arm assembly coupled to the first crosshead assembly and a second gripping arm assembly coupled to the second crosshead assembly.

6. The load frame assembly of claim 5 wherein the first gripping arm assembly includes a grip dovetail pin and the first gripping arm assembly includes an upper gripping arm and a lower gripping arm couplable to the upper gripping arm, at least one of the upper gripping arm and the lower gripping arm including a grip dovetail configured to interface with the grip dovetail pin coupling the respective gripping arm thereto.

7. The load frame assembly of claim 6 wherein the second gripping arm assembly includes a grip dovetail pin and the second gripping arm assembly includes an upper gripping arm and a lower gripping arm couplable to the upper gripping arm, at least one of the upper gripping arm and the lower gripping arm including a grip dovetail configured to interface with the grip dovetail pin coupling the respective gripping arm thereto.

8. The load frame assembly of claim 7 wherein each of the upper and lower gripping arms of the first gripping arm assembly include a dovetail structurally configured to engage the grip dovetail pin of the first crosshead assembly.

9. The load frame assembly of claim 8 wherein each of the upper and lower gripping arms of the second gripping arm assembly include a dovetail structurally configured to engage the grip dovetail pin of the second crosshead assembly.

10. The load frame assembly of claim 5 wherein the first gripping arm assembly and the second gripping arm assembly is vertically adjustable.

11. The load frame assembly of claim 1 wherein the displacement sensor comprises a capacitive sensor, wherein displacement of the respective at least one of the first crosshead and second crosshead results in a change in capacitance.

12. The load frame assembly of claim 1 further comprising:
a second servomotor coupled to the frame assembly;
a second actuator assembly having a ball screw assembly, with a ball screw and a ball screw nut rotatably coupled to the ball screw, one of the ball screw and the ball screw nut being coupled to the frame assembly to preclude linear movement therealong, and coupled to the second servomotor to facilitate rotation thereof about an axis;
the second crosshead assembly being coupled to one of the ball screw and the ball screw nut of the second actuator assembly.

13. The load frame assembly of claim 12 wherein at least one of the load cell and the displacement sensor is coupled to the control system of the second servomotor to provide feedback as to the position of the respective one of the first and second crosshead.

\* \* \* \* \*